United States Patent [19]
Trost et al.

[11] Patent Number: 5,919,948
[45] Date of Patent: Jul. 6, 1999

[54] ASYMMETRIC LIGANDS USEFUL FOR TRANSITION METAL CATALYZED BOND FORMING REACTIONS AND EPOXIDE REACTIONS THEREWITH

[75] Inventors: Barry M. Trost, Los Altos Hills; Richard C. Bunt, Redwood City, both of Calif.

[73] Assignee: The Board of Trustees of the Leland Stanford Junior University, Stanford, Calif.

[21] Appl. No.: 08/487,023

[22] Filed: Jun. 7, 1995

Related U.S. Application Data

[63] Continuation-in-part of application No. 08/308,839, Sep. 19, 1994, abandoned, which is a continuation-in-part of application No. 07/804,783, Dec. 9, 1991, abandoned.

[51] Int. Cl.[6] .................................................. C07C 29/00
[52] U.S. Cl. .......................................... 548/478; 548/479
[58] Field of Search ..................... 549/478, 479

[56] References Cited

U.S. PATENT DOCUMENTS 4,209,468  6/1980  Shulman .
4,705,895  11/1987  Okano et al. .

OTHER PUBLICATIONS

Morrison and Masler, *J. Org. Chem.*, 39:2, pp. 270–272 (1974).
Masuda and Stille, *J. Am. Chem. Soc.*, 100:1, pp. 268–272 (1978).
LaFont et al., *J. Chem. Research* (S), 234, p. 117 (1982).
Riley, *J. Organomet. Chem.*, 234, pp. 85–97 (1982).
MacNeil et al., *J. Am. Chem. Soc.*, 103, pp. 2273–2280 (1981).
Fryzuk and Bosnich, *J. Am. Chem. Soc.*, 99:19, pp. 6262–6267 (1977).
Roberts and Wild, *J. Am. Chem. Soc.*, 101:21, pp. 6254–6260 (1979).
Bergstein et al., *Synthesis*, 76, pp. 76–78 (1981).
Juge et al., *Tetrahedron Letters*, 31:44, pp. 6357–6360 (1990).
Imamoto et al., *J. Am. Chem. Soc.*, 112, pp. 5244–5252 (1990).
Knowles et al., *J. Am. Chem. Soc.*, 97:9, pp. 2567–2568 (1975).
Fukuda et al., *Tetrahedron Letters*, 31:49, pp. 7185–7188 (1990).
Onuma et al., *Chem. Letters*, pp. 905–908 (1979).
Achiwa, *J. Am. Chem. Soc.*, 98:25, pp. 8265–8266 (1976).
Beck and Menzel, *J. Organomet. Chem.*, 133, pp. 307–310 (1977).
Kagen and Dang, *J. Am. Chem. Soc.*, 94:18, pp. 6429–6433 (1972).
Aviron–Violet et al., *J. Mol. Catal.*, 5, pp. 41–50 (1979).
Dang et al., *J. Organomet. Chem.*, 91, pp. 105–115 (1975).
Glaser et al., *Tetrahedro Letters*, 52, pp. 4639–4642 (1977).
Kreuzfeld and Döbler, *React. Kinet. Catal. Lett.*, 16:2–3, pp. 229–232 (1981).
Pracejus and Pracejus, *J. Mol. Catal.*, 24, pp. 227–230 (1984).
Samuel et al., *Nouv. J. Chim*, 5:1, pp. 15–20 (1981).
Lauer et al., *J. Organomet. Chem.*, 177, pp. 309–312 (1979).
Tanaka et al., *Chem. Lett.*, pp. 1115–1118 (1975).
Alario et al., *J. Chem. Soc., Chem. Com.*, pp. 202–203 (1986).
Takaya et al., *Org. Syn.*, 67, pp. 20–32 (1989).
Grubbs and DeVries, *Tetrahedron Letters*, 22, pp. 1879–1880 (1977).
Trost and Murphy, *Organometallics*, 4, pp. 1143–1145 (1985).
Tamao et al., *Tetrahedron Letters*, 16, pp. 1389–1392 (1977).
Miyano et al., *Chem. Lett.*, pp. 729–730 (1980).
Miyano et al., *Bull. Chem. Soc. Jpn.*, 57, pp. 2171–2176 (1984).
Uehara et al., *Chem. Lett.*, pp. 441–444 (1983).
Hayashi et al., *Bull. Chem. Soc. Jpn.*, 53, pp. 1138–1151 (1980).
Hayashi and Kumada, *Acc. Chem. Res.*, 15, pp. 395–401 (1982).
Johnson et al., *J. Mol. Catal.*, 12, pp. 37–40 (1981).
Petit et al., *Nouv. J. Chim.*, 7:10, pp. 593–596 (1983).
Pracejus and Pracejus, *Tetrahedron Letters*, 39, pp. 3497–3500 (1977).
Fiorini et al., *J. Mol. Catal.*, 4, pp. 125–134 (1978).
Consiglio and Waymouth, *Chem. Rev.*, 89, pp. 257–276 (1989).
Noyori and Kitamura, "Enantioselective Catalysis with Metal Complexes. An Overview," in *Modern Synthetic Methods*, vol. 5, Scheffold, ed., Springer–Verlag: Berlin, pp. 115–198 (1989).
Noyori, *Chem. Soc. Rev.*, 18, pp. 187–208 (1989).

(List continued on next page.)

*Primary Examiner*—Robert Gerstl
*Attorney, Agent, or Firm*—Majestic, Parsons, Siebert & Hsue

[57] ABSTRACT

A novel ligand having the Formula 1 structure has proved remarkably successful in the amination of butadiene monoepoxide, which is a potentially desirable substrate for an asymmetric synthesis providing access to each enantiomer of vinylglycinol.

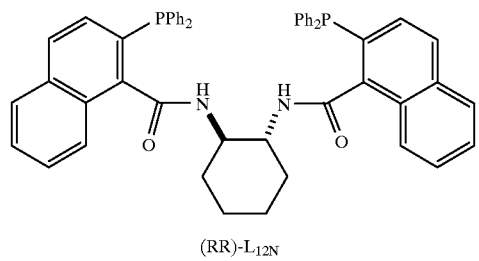

(RR)-L$_{12N}$

This and other ligands described are useful for chiral induction of bond forming reactions with an epoxide substrate.

9 Claims, No Drawings

OTHER PUBLICATIONS

Ojima et al., *Tetrahedron Letters,* 45:22, pp. 6901–6939 (1989).

Blystone, *Chem. Rev.,* 89:8, pp. 1663–1679 (1989).

Brunner, "Enantioselective Syntheses with Optically Active Transition Metal Catalysts," chapter in *The Chemistry of the Metal–Carbon Bond,* vol. 5, Hartley, ed., and John Wiley & Sons: New York, pp. 109–146 (1989).

Brunner, *Synthesis,* pp. 645–653 (1988).

Merlic, "Transition Metal Mediated Asymmetric Allylic Alkylations," chapter 2 in *Molybdenum Catalyzed Allylic Alkylations,* Ph. D. Dissertation, University of Wisconsin, Madison, pp. 780–79 (1988).

Kitamura et al., *Tetrahedron Letters,* 28:40, pp. 4719–4720 (1987).

Trost et al., *J. Am. Chem. Soc.,* 110, pp. 621–622 (1988).

Trost and Van Vranken, *J. Am. Chem. Soc.,* 113: pp. 6317–6318 (1991).

Fiorini and Giongo, *J. Mol. Catal.,* 5, pp. 303–310 (1979).

Trost and Van Vranken, *Angewandte Chemie,* 31:2, pp. 228–230 (1992).

Trost et al., *J. Am. Chem. Soc.,* 114, pp. 9327–9343 (1992).

Whitesell, *Chem. Rev.,* 89, pp. 1581–1590 (1989).

ASYMMETRIC LIGANDS USEFUL FOR TRANSITION METAL CATALYZED BOND FORMING REACTIONS AND EPOXIDE REACTIONS THEREWITH

This invention is a continuation-in-part of application U.S. Ser. No. 08/308,839, filed Sep. 19, 1994, which is a continuation-in-part of U.S. Ser. No. 07/804,783, filed Dec. 9, 1991, both abandoned.

This invention was made with Government support under Grants CHE 9122761 from the National Science Founation and Grant NIH GM 13598 from the National Institutes of Health. The Government has certain rights in this invention.

FIELD OF THE INVENTION

The present invention generally relates to use of ligands for transition metal catalyzed reactions, and more particularly relates to a new class of asymmetric ligands preferably derived from 2-diphenylphosphino-naphthoic acid as an ester or amide from chiral alcohols and chiral amines, and epoxide reactions with such ligands.

BACKGROUND OF THE INVENTION

The importance of enantiomerically pure compounds is a result of the enantiomeric selectivity of biology. Because biology is based on a particular enantiomer, L-amino acids, enantiomeric recognition is an inherent component of biological processes. A prototypical example of the enantiomeric selectivity is the case history of thalidomide. Thalidomide was a widely prescribed drug that was eventually removed from the market because of unforeseen side effects. Administered as a racemic mixture, the R-isomer is a sleep aid whereas the S-isomer is a potent teratogen. Thalidomide is not unique in having only one enantiomer of optically active compound that exhibits the desired pharmacological effect. However, because of the difficulties in synthesizing enantiomerically pure compounds, racemic mixtures are often used.

A relatively new and promising approach to enantioselective synthesis, where the chiral product is enriched in either enantiomer, is the use of optically active transition metal compounds as catalysts. Enantioselective catalysis in general hinges upon the ability to minimize the energy barrier ($\Delta\Delta G\ddagger$) of the desired enantiomer product relative to the other. Small energy differences translates into relatively large differences in enantiomeric excess. For example, a 1.3 kcal/mole difference in transition state energies results in an enantiomeric excess of 80%.

Enantiomeric excess ("e.e.") is the enrichment of one enantiomer over the other from the expected value. For example, if the optically active product contains equal amounts of enantiomers, then the enantiomeric excess is 0. If the ratio is 70:30, then the enantiomeric excess is 40%, and if the ratio is 90:10, then the enantiomeric excess is 80% and so on.

Transition metals are good candidates for enantioselective catalysis because of their ability to mediate a wide variety of bond-forming and bond-breaking processes. Because transition metals do not display the necessary specificity, the conjunctive use of chiral ligands or auxiliaries is essential for enantioselective catalysis. Coordinated to the metal, the metal-ligand complex binds to the prochiral precursor and in so doing induces the formation of one enantiomer over the other. Because both sterics and electronics are readily modified, phosphines are often preferred. As a result, a large number of chiral phosphine ligands have been prepared. However, only a few have gained popular use probably because of difficulties in synthesis or inadequate enantiomeric excesses or a combination of both.

One area where enantiomerically pure compounds are useful is where an enantiomerically pure vinylglycinol (or vinylglycine) is used as a synthetic building block for biologically important targets, such as various antibiotic enzyme inhibitors, calmodulin inhibitors, and others. EP 529,601, published Mar. 3, 1993, inventors Fuelling and Kretzschmar is an example of optically active vinylglycine compounds, useful as enzyme inhibitors, antibacterials, and cytostatics. These optically active vinylglycines are produced by enzymatically resolving racemic vinylglycine; however, a simple asymmetric synthesis that would provide access to both enantiomers is most desirable.

At present, the most effective synthesis of vinylglycine has begun with amino acids, which restricts ready availability to the L-enantiomer. A simple asymmetric synthesis providing access to each enantiomer, as desired, would be quite useful.

SUMMARY OF THE INVENTION

In one aspect of the present invention, a ligand is provided that is useful for enantioselective transition metal catalysis and comprises a metal binding moiety that is attached to a chiral backbone. The chiral backbone is derived from a chiral alcohol or amine. The metal binding portion has at least one metal binding moiety with the structure

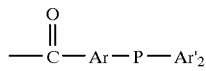

wherein Ar is a fused ring and Ar' is an aryl or a heteroaryl with a single ring or fused rings.

A particularly preferred ligand of the invention has the Formula 1 structure, and is hereinafter sometimes referred to as "(RR)-L$_{12N}$" as an abbreviation of (−)−1R,2R-diamino-1N,2N-bis(2'-diphenyl-phosphino-1'-naphthoyl) cyclohexane.

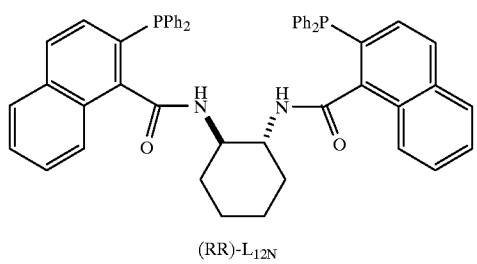

(RR)-L$_{12N}$

This chiral ligand embodiment has proved remarkably successful in the amination of butadiene monoepoxide, which is one type of epoxide and a potentially desirable starting material (or substrate) for an asymmetric synthesis providing access to each enantiomer of vinylglycinol. Therefore, the ligand (RR)-L$_{12N}$ should prove useful in syntheses of many biologically important targets.

In another aspect of this invention ligands are useful for chiral induction of bond forming reactions with an epoxide substrate.

DETAILED DESCRIPTION OF THE PREFERRED EMBODIMENTS

Transition metal catalyzed bond forming reactions (with which ligands in accordance with the invention are useful)

are well known in the art, and among the recent reviews describing such reactions are:

(1) Consiglio et al., "Enantioselective Homogeneous Catalysis Involving Transition-Metal-Allyl Intermediates", *Chem. Rev.*, 1989, 89, 257–276;

(2) Noyori et al., "Enantioselective Catalysis with Metal Complexes. An Overview." *Modern Synthetic Methods, Vol.* 5, Scheffold, ed., Springer-Verlag: Berlin, 1989, 199–248;

(3) Noyori, R., "Chemical Multiplication of Chirality: Science and Applications," *Chem. Soc. Rev.*, 1989, 18, 1987–208;

(4) Ojima et al., "Recent Advances in Catalytic Asymmetric Reasons Promoted by Transition Metal Complexes", *Tetrahedron*, 1989, 45, 6901–6939;

(5) Blystone, S. L., "Synthetic Applications of Enantioselective Organotransition-Metal-Mediated Reactions," *Chem. Rev.*, 1989, 89, 1663–1679;

(6) Brunner, H. T., "Enantioselective Synthesis with Optically Active Transition Metals," Chapter 4 in *The Chemistry of the Metal-Carbon-Bond, Vol. 5*, Hartley, ed., John Wiley & Sons: New York, 1989, 109–146;

(7) Brunner, H. T., "Enantioselective Synthesis with Optically Active Transition Metal Catalysts," *Synthesis*, 1988, 645–654; and (8) Merlic, C. A., "Ch. 3. Transition Metal-Mediated Asymmetric Allylic Alkylations," *Molybdenum Catalyzed Allylic Alkylations*, Ph.D., University of Wisconsin, Madison, 1988, pp. 4–79.

Among such transition metal catalyzed bond forming reactions are those involving palladium. One application of this invention is to use epoxide as substrates in bond forming reactions with ligands as will now be described.

Chiral ligands for enantioselective catalysis with epoxide substrates may be derived as reaction products from 2-diphenylphosphino benzoic acid (2-DPPBA) or 2-diphenylphosphinonaphthoic acid (sometimes designated "the acid precursors") and either chiral alcohols or chiral amines.

These acid precursors may be derivatized with any of a wide variety of chiral alcohols or chiral amines, such as by coupling in the presence of dicyclohexylcarbodiimide (DCC). Among the inexpensive and readily available chiral diols useful for derivatizing 2-diphenylphosphinobenzoic acid are mannitol and tartaric acid.

The aromatic carboxylic acid of the acid precursors carry a diarylphosphino (or a diheteroarylphosphino) substituent. Thus, the necessary phosphino substituent and the carbonyl substituent may be on an aryl, a fused ring, or heteroaryl that is further substituted by a moderately or weakly activating or deactivating group, such as with an alkyl group (branched or unbranched) usually with not greater than about ten carbons, a halide, or an alkoxy (e.g., —$OCH_3$, —$OC_2H_5$, etc.). In the instance of fused rings, the necessary phosphino substituent and the carboxyl substituent preferably are 1,2 on the one ring. Among the heteroatoms that can form the single or fused heteroaryl ring of the aromatic carboxylic acid from which the ligands may be derived are nitrogen, oxygen, and sulfur. Illustrative, suitable heteroaryl carboxylic acids on which the diarylphosphino (or diheteroarylphosphino) group can be substituted include compounds such as

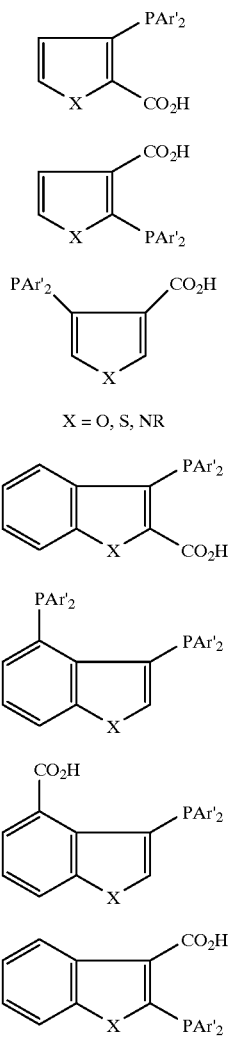

X = O, S, NR

As is illustrated by the embodiment derived from 2-DPPBA, the carboxyl group and the diphenylphosphino group are preferably in an ortho relationship, which serves best for the ligand function.

The carboxylic acid functionality and the alcohol/amine functionalities may be exchanged to generate ligands that we call "invertomers."

Thus, to summarize, the ligands can be generally described as a functional module (forming a chiral pocket) joined by an ester or an amide linkage to a structural module we term a chiral scaffold. For one class of ligands, the functional module, which is a metal binding component, has the structure

where Ar is an aromatic ring substituent. The functional module is joined by an ester or an amide linkage to the structural module. The structural module can be derived from any chiral alcohol or chiral amine having one or more stereogenic centers. A particularly preferred embodiment of the structural module is derived from a C2 symmetrical bis alcohol or a bis amine.

Table 1 summarizes a variety of ligands with single rings in the "Ar" of the metal binding moiety, which are further described in copending U.S. application Ser. No. 08/487,039, filed concurrently and of common assignment herewith.

TABLE 1

| Ligand Embodiment | Structure of the Ligand | e.e. from Reaction 1 |
| --- | --- | --- |
| (+)-6.24 | | 40% |
| (+)-6.25 | | 64% |
| (−)-6.26 | | 61% |
| (+)-6.27 | | 80% |

TABLE 1-continued

| Ligand Embodiment | Structure of the Ligand | e.e. from Reaction 1 |
|---|---|---|
| (−)-6.27 | [structure: 1,2-diphenyl-1,2-ethanediamine bis(2-diphenylphosphinobenzamide)] | 79% |
| (−)-6.28 (also designated as "(RR)—L$_B$") | [structure: trans-1,2-diaminocyclohexane bis(2-diphenylphosphinobenzamide)] | 78% |
| (+)-6.29 | [structure: N-benzyl-3,4-bis(2-diphenylphosphinobenzoyloxy)succinimide] | 75% |
| (−)-6.31 | [structure: N-benzyl bis(2-phenyl-2-(2-diphenylphosphinobenzoyloxy)ethyl)amine] | 60% |

TABLE 1-continued

| Ligand Embodiment | Structure of the Ligand | e.e. from Reaction 1 |
|---|---|---|
| (+)-6.32 | 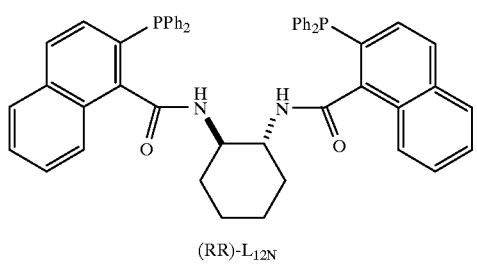 | 88.1% |

Preferred ligands have Ar as a fused ring. A particularly preferred ligand of this invention has the Formula 1 structure, and is hereinafter sometimes referred to as "(RR)-$L_{12N}$" as an abbreviation of (−)−1R,2R-diamino-1N,2N-bis (2'-diphenylphosphino-1'-naphthoyl)cyclohexane.

(RR)-$L_{12N}$

This chiral ligand embodiment has proved remarkably successful in the amination of butadiene monoepoxide, which is a potentially desirable starting material for an asymmetric synthesis providing access to each enantiomer of vinylglycinol. Thus, the ligand (RR)-$L_{12N}$ should prove useful in syntheses of many biologically important targets.

Without being limited by theory, we believe that the (RR)-$L_{12N}$ embodiment has dramatic effects on asymmetric induction by rigidifying the mode of linkage between the chiral scaffold and the "chiral pocket" in which reaction occurs by freezing rotations in the linker. Thus, we believe that the (RR)-$L_{12N}$ ligand has a relatively tight "chiral pocket" formed by the two metal binding moieties held in position by the chiral scaffold. Rigidifying the carboxylate unit by using a ligand constructed from the diamine and 2-diphenylphosphino-1-naphthoic acid had a dramatic effect in enhancing selectivity. This preferred ligand embodiment gave an outstanding result in the addition of phthalimide to 3,4-epoxy-1-butene (butadiene monoepoxide), and provided the protected vinylglycinol quantitatively with an enantiomeric ratio (e.r.) of 99:1. Since vinylglycinol of high enantiomeric purity has now been made available simply through use of the inventive ligand, there is provided a ready entry into either enantiomeric series for syntheses of biologically interesting and important targets.

The Formula 1 preferred ligand was prepared along with two other similar compounds as a study in rigidification and to focus on how the chiral scaffold represented by the diaminocyclohexane unit communicates with the conformationally chiral space created by the diphenylphosphino unit. These two other compounds are illustrated by Formulas 2 and 3, and are respectively designated "(RR)-$L_{21N}$" and "(RR)-$L_{23N}$."

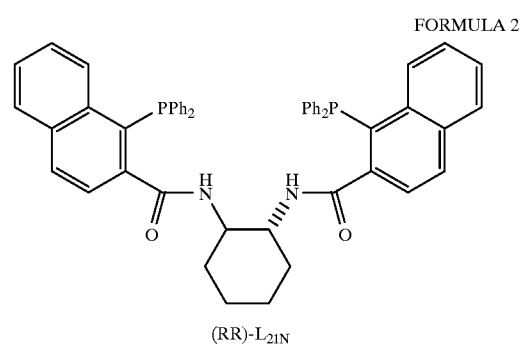

FORMULA 2

(RR)-$L_{21N}$

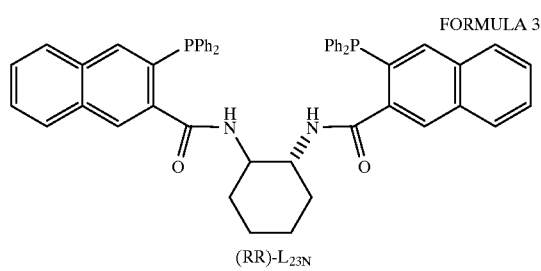

FORMULA 3

(RR)-$L_{23N}$

To compare these new ligands, we explored the alkylation in Eq. 1 as our standard.

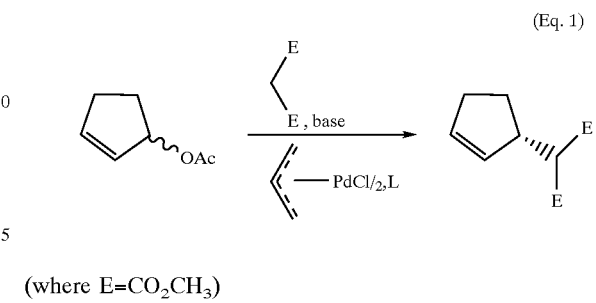

(Eq. 1)

(where E=$CO_2CH_3$)

For further comparison, we used the Formula 1–3 ligands as well as the ligand with a single Ar in each metal binding moiety and sometimes referred to as "(RR)-$L_B$."

The (RR)-$L_{23N}$ ligand and the single Ar (RR)-$L_B$ ligand, were found to behave similarly and to give very high er's with cesium carbonate as base in methylene chloride (entries 4 and 8) in Table 2. Restricting the diphenylphosphino unit as in (RR)-$L_{21N}$ effectively destroyed the chiral recognition. Restricting the carboxylate group maintained a reasonable level of chiral recognition, although somewhat less than for (RR)-$L_B$ or (RR)-$L_{23N}$.

In contrast to (RR)-$L_B$ or (RR)-$L_{23N}$, we explored the reaction of the acyclic substrate shown in Eq. 2 with dimethyl malonate for which the maximum er previously recorded in the literature was 85:15.

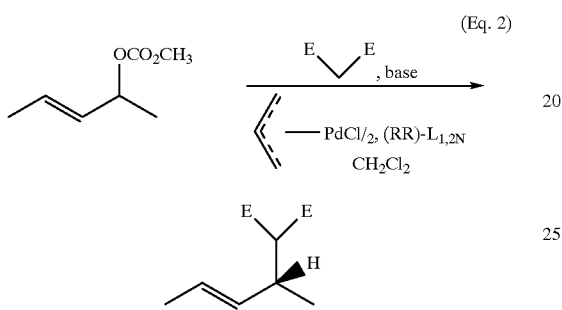

(Eq. 2)

Using the (RR)-$L_{12N}$ ligand, the er of product produced in Eq. 2 was 70:30 for the sodium salt (base was sodium hydride) but 93:7 for the cesium salt (base was cesium carbonate), the highest recorded in the literature.

The most dramatic result of the new ligand (RR)-$L_{12N}$ occurred for the type of chiral recognition required in the case of the epoxide shown (Eq. 3).

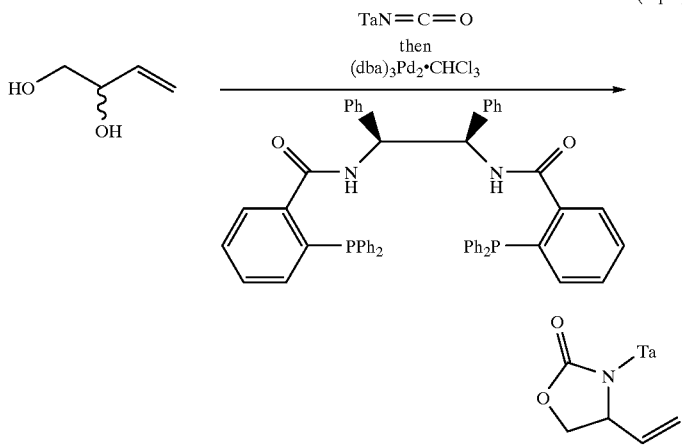

(Eq. 3)

Adding neat epoxide to a mixture of phthalimide (110 mol %), sodium carbonate (5 mol %), II-allylpalladium chloride dimer (2.5 mol %), and (RR)-$L_{12N}$ (7.5 mol %) in dichloromethane all at ambient temperature gave a 99% isolated yield of >75:1 ratio of proximal to distal products. This 99% isolated yield is in contrast to the 30–40% yield with no ligand (and in comparison to 9:1 ratio of proximal to distal). The er was assayed by conversion to the )-methylmandelate ester and hplc analysis and found to 99:1 (Eq. 4).

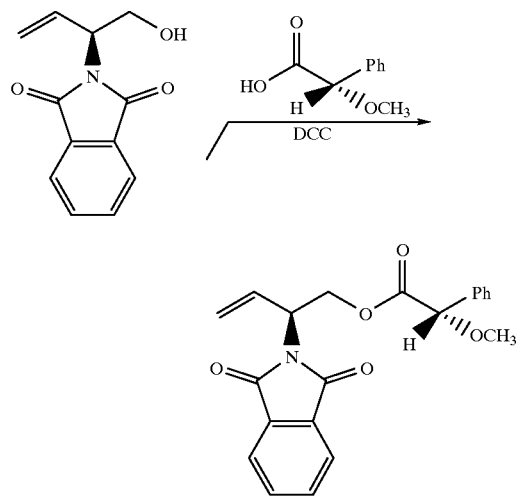

(Eq. 4)

Thus, vinylglycinol of high enantiomeric purity is available very simply from racemic 3,4-epoxy-1-butene by use of the new (RR)-$L_{12N}$ ligand. Since the conversion of vinylglycinol to vinylglycine is also known, this route also constitutes a synthesis of the latter as well.

In contrast to previous syntheses relying on the natural amino acids as precursors, this route provides ready entry into either enantiomeric series. For this type of asymmetric induction, which requires a kinetic bias for reaction of one diastereomeric II-allylpalladium complex of a rapidly interconverting pair, rigidifying the carboxylate group had a dramatic effect in enhancing the selectivity. This same ligand does very well in discriminating the enantiotopic termini of the 1,3-dimethylallyl system (cf Eq. 2). The nature of the "chiral cavity" of (RR)-$L_{12N}$ is quite distinct from the other ligands.

As earlier noted, to compare the naphthyl derived ligands to each other (and to a phenyl ligand), the alkylation of 2-cyclopentenyl acetate with dimethyl malonate (Eq. 1) was performed with each ligand under four sets of conditions. Both sodium hydride and cesium carbonate were used as the base in tetrahydrofuran (THF) and dichloromethane (DCM) respectively, and these data are summarized by Table 2.

TABLE 2

| Entry | Ligand | Base | Solvent | Yield | $[\alpha]_D$ | ee (%) | Method[a] | er (S:R) |
|---|---|---|---|---|---|---|---|---|
| 1 | (RR)-$L_B$ | NaH | THF | 73 | −28.2° | 33 | op. rot. | 67:33 |
| 2 | (RR)-$L_B$ | NaH | DCM | 91 | −43.6° | 47 | NMR | 74:26 |
| 3 | (RR)-$L_B$ | $Cs_2CO_3$ | THF | 89 | −55.7° | 65 | op. rot. | 83:17 |
| 4 | (RR)-$L_B$ | $Cs_2CO_3$ | DCM | 82 | −81.0° | 97 | NMR | 99:1 |
| 5 | (RR)-$L_{23N}$ | NaH | THF | 65 | −21.3° | 25 | op. rot. | 63:37 |
| 6 | (RR)-$L_{23N}$ | NaH | DCM | 85 | −23.4° | 28 | NMR | 64:36 |
| 7 | (RR)-$L_{22N}$ | $Cs_2CO_3$ | THF | 47 | −45.7° | 51 | NMR | 76:24 |
| 8 | (RR)-$L_{23N}$ | $Cs_2CO_3$ | DCM | 91 | −82.7° | 96 | NMR | 98:2 |
| 9 | (RR)-$L_{12N}$ | NaH | THF | 99 | −58.2° | 68 | op. rot. | 53:47 |
| 10 | (RR)-$L_{12N}$ | NaH | DCM | 96 | −75.3° | 87 | NMR | 58:42 |
| 11 | (RR)-$L_{12N}$ | $Cs_2CO_3$ | THF | 76 | −33.6° | 39 | op. rot. | 53:47 |
| 12 | (RR)-$L_{12N}$ | $Cs_2CO_3$ | DCM | 90 | −68.7° | 80 | NMR | 62:38 |
| 13 | (RR)-$L_{21N}$ | NaH | THF | 63 | −5.3° | 6 | op. rot. | 84:16 |
| 14 | (RR)-$L_{21N}$ | NaH | DCM | 88 | −13.0° | 15 | op. rot. | 94:6 |
| 15 | (RR)-$L_{21N}$ | $Cs_2CO_3$ | THF | 79 | −4.6° | 5 | op. rot. | 70:30 |
| 16 | (RR)-$L_{21N}$ | $Cs_2CO_3$ | DCM | 87 | −18.6° | 23 | NMR | 90:10 |

[a]For ee's determined by optical rotation a value of −85.2° was used for the homochiral compound.

Comparing entries 1–4 with entries 5–8 one observes that the (RR)-$L_{23N}$ ligand is generally similar or in some cases somewhat worse than (RR)-$L_B$. Entries 9–12 show that the preferred ligand embodiment (RR)-$L_{12N}$ has a distinctly different selectivity profile than (RR)-$L_B$. Finally, entries 13–16 show an extremely poor enantioselectivity obtained with (RR)-$L_{21N}$. The effect of the base seems largely due to the differences in the counter ion, but some effect of the carbonate rather than hydride base cannot be excluded and likely plays a minor role.

The Equation 3 reaction is butadiene monoepoxide, which is of an epoxide-type, or class, that can be generally viewed as having the following structure (where R is H, alkyl, aryl, or a functional group and R' is H, alkyl, alkenyl, aryl, or a functional group):

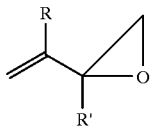

(Ep 1)

Illustrative alkyls and alkenyls for R are $C_{1-20}$ carbons, linear or branched, with one or more unsaturated bonds (triple or double). Illustrative aryls are phenyl and heteroaryls (e.g. furyl, pyrroyl). Illustrative functionalized species are carboxylic acid derivatives (e.g. esters, amides), halides, ketones, and nitriles. However, the ligands, such as derived from 2-diphenylphosphinobenzoic acid or from 2-diphenylphosphinonaphthoic acid, either as an ester or amide from chiral alcohols and chiral amines, can be used for chiral induction of another class, or type, or epoxide as substrate where this second class may be generally represented by the following structure (where R is as described for the first class):

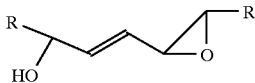

(Ep 2)

Among the applications for chiral induction with epoxides of the second class are, for example, syntheses of carbohydrates, monosaccharide portions of antitumor agents (e.g. calichemycin, daunomycin), glycosidase inhibitors, and antifungal nucleosides (such as polyoxins).

Preparation of the preferred ligand embodiment (RR)-$L_{12N}$ (Part A of Example 1) and its use in synthesizing vinylglycinol of high enantiomeric purity from racemic 3,4-epoxy-1-butene (Part B of Example 1) will now be illustrated. Preparation of a benzoic acid derived ligand (Part A of Example 2) and its use with the second epoxied class (Part B of Example 2) will then be illustrated.

EXAMPLE 1

Part A: 2-diphenylphosphino-1-naphthoic acid

To a 250 ml round bottom flask was added 2.85 g (7.7 mmol) 2-diphenylphosphino-1-naphthoic acid methyl ester, 14.8 g (47.0 mmol) Ba(OH)$_2$.8H$_2$O, the flask purged with nitrogen, and 47 ml MeOH added. The reaction was heated at reflux overnight (25 hours). After cooling to room temperature, the reaction mixture was neutralized with 200 ml 1N NaHSO$_4$ (aq) and extracted 4×100 ml dichloromethane. The combined organic phases were dried over Na$_2$SO$_4$ and concentrated in vacuo. The yellow residue was absorbed onto ~8 g silica gel and filtered through a short column of silica gel (4 cm×6 cm, 100% ethyl acetate) to give 2.42 g (88%) of a yellow solid (mp 190°–192° C. dec.) which was used without further purification.

$R_f$ 0.56 (100% ethyl acetate).

IR (Kbr): 3414, 3074, 3057, 1685, 1434, 1287, 1252 cm$^{-1}$.

$^1$H NMR (300 MHz, DMSO-d$_6$) δ8.0 (d, J=8.2 Hz, 1H), 7.82 (d, J=8.0 Hz, 1H), 7.78 (d, J=8.5 Hz, 1H), 7.5–7.6 (m, 2H), 7.25 (m, 10H), 7.15 (dd, J=8.3, 2.8 Hz, 1H).

$^3$C NMR (75 MHz, DMSO-d$_6$) δ170.4 (d, J=3.4 Hz), 141.6 (d, J=38.0 Hz), 137.0 (d, J=10.7 Hz), 133.1 (d, J=19.1 Hz), 132.1, 131.9, 130.7 (d, J=17.0 Hz), 129.6, 129.3, 129.2, 128.9 (d, J=6.9 Hz), 128.7, 128.5, 127.8, 125.5.

Analysis: Calc'd for C, 77.52; H, 4.81; P, 8.69. Found: C, 77.38; H, 5.00; P, 8.51.

(−)-1R,2R-diamino-1N,2N-bis(2'-diphenylphosphino-1'-naphthoyl)cyclohexane ("(RR)-$L_{12N}$")

To a 100 ml round bottom flask was added 1.90 g (5.33 mmol) 2-diphenylphosphino-1-naphthoic acid and 42 ml dichloromethane. After cooling to 0° C., 1.78 g (17.6 mmol) triethyl amine was added followed by 1.58 g (5.87 mmol) diphenylchlorophosphite added dropwise over 2–3 minutes. After warming to room temperature over 5 hours, the mixture was transferred via cannula to solution of 304 mg (2.66 mmol) (1R,2R)-diaminocyclohexane and 30.5 mg (0.25 mmol) 4-dimethylaminopyridine in 11 ml dichloromethane and stirred overnight. The reaction mixture was diluted with 50 ml dichloromethane and washed 1×50 ml saturated aqueous sodium bicarbonate and dried over sodium sulfate and concentrated in vacuo. The crude product was purified by flash chromatography on silica gel (4.5 cm×11 cm, 25% ethyl acetate in hexanes) to give 1.07 g (51%) of a white solid which was crystallized from chloroform/hexanes as a white powder (mp 148°–150° C.).

$[\alpha]_D$=+13.94° (c 1.19, $CH_2Cl_2$).

$R_f$ 0.64 (50% ethyl acetate in hexanes).

IR (solution $CDCl_3$): 3412, 3072, 3057, 2938, 2862, 1648, 1602, 1510, 1435, 1313, 1256, 1237, 1091, 1027 $cm^{-1}$.

$^1$H NMR (300 MHz, $CDCl_3$) δ7.8 (d, J=8.2 Hz, 2H), 7.7 (d, J=9.1 Hz, 2H), 7.6 (d, J=8.9 Hz, 2H), 7.2–7.4 (m, 22H), 7.0 (m, 4H), 6.6 (d, J=5.5 Hz, 2H), 3.8 (m, 2H), 2.3 (m, 2H), 1.7 (m, 2H), 1.2–.13 (m, 4H).

$^{13}$C NMR (75 MHz, $CDCl_3$) δ169.2 (d, J=4.2 Hz), 142.0 (d, J=34.2 Hz), 136.85 (d, J=11.3 Hz), 136.81 (d, J=11.3 Hz), 133.5 (d, J=19.6 Hz), 133.4 (d, J=19.3 Hz), 133.3, 131.3 (d, J=18.1 Hz), 129.9 (d, J=7.9 Hz), 129.4, 129.2, 128.7, 128.7, 128.6, 128.5, 128.4 (d, J=6.7 Hz), 127.7, 127.2, 126.9, 125.6, 54.7, 31.5, 24.4.

Analysis: Calc'd for C, 78.97; H, 5.61; N, 3.54; P, 7.83. Found: C, 78.76; H, 5.86; N, 3.38; P, 7.67.

Part B: Asymmetric alkylation of butadiene monoepoxide with phthalimide

To a 20 ml test tube was added 9.1 mg (0.025 mmol) [$η^3C_3H_5PdCl$ ]$_2$, 59.3 mg (0.075 mmol) (–)-1R,2R-diamino-1N,2N-bis(2'-diphenylphosphino-1'-naphthoyl) cyclohexane, 5.0 mg (0.05 mmol) sodium carbonate, and 162 mg (1.10 mmol) phthalimide. The flask was purged with nitrogen, 10 ml dichloromethane added, and stirred 10 minutes, color to bright yellow. Then, 70.1 mg (1.00 mmol) butadiene monoepoxide (3) was added, color to clear, and the reaction stirred at room temperature for 2.5 hours at which time the bright yellow color had returned. The reaction mixture was concentrated in vacuo and purified by flash chromatography on silica gel (3 cm×12 cm, 60% diethyl ether in hexanes) to give 216.2 mg (99%) of the 1,3 addition product as a white solid (mp 61°–62° C.) in 98% ee as determined by HPLC of the (S)-methoxyphenylacetate ester.

$[\alpha]_D$=–71.11° (c 3.06, $CH_2Cl_2$).

$R_f$ 0.65 (100% diethyl ether).

IR (film from $CDCl_3$): 3450, 3086, 2945, 2888, 1767, 1704, 1644, 1614, 1469, 1386, 1226, 1173, 1107, 1060, 1020 $cm^{-1}$.

$^1$H NMR (300 MHz, $CDCl_3$) 7.8 (m, 2H), 7.7 (m, 2H), 6.1 (ddd, J=17.3, 10.2, 6.9 Hz, 1H), 5.3 (m, 2H), 4.9 (m, 1H), 4.1–4.2 (m, 1H), 3.9–4.0 (m, 1H), 2.9 (bs, 1H).

$^{13}$C NMR (75 MHz, $CDCl_3$) 168.4, 133.9, 132.0, 131.4, 123.0, 118.6, 61.7, 55.5.

Analysis: Calc'd for C, 66.35; H, 5.11; N, 6.45. Found: C, 66.60; H, 5.33; N, 6.65.

Preparation of 2-phthalamido-3-butenyl (S)-methoxyphenylacetate

To a 3 ml test tube was added 10.9 mg (0.05 mmol) 2-phthalamido-3-butenol, 10.1 mg (0.06 mmol) (S)-methoxyphenylacetic acid, 14.4 mg (0.07 mmol) dicyclohexylcarbodiimide, 0.5 mg (0.005 mmol) 4-dimethylaminopyridine, and 0.5 ml dichloromethane. The reaction was stirred at room temperature overnight and then filtered through cotton. The product was purified by flash chromatography on silica gel (1 cm×12 cm, 40% diethyl ether in pentane) to give 18.0 mg (98%) of the title compound as a clear oil in 98% de, as determined by HPLC analysis (Dynamax 60A analytical, 15% ethyl acetate in hexanes, 1.0 ml/min, λ=254 nm, $T_R$=22.3, 23.4 min).

$[\alpha]_D$=+4.24° (c 1.80, $CH_2Cl_2$).

$R_f$ 0.62 (30% ethyl acetate in hexanes).

Spectral data taken from racemate (RB-XI-8)

IR (film from $CDCl_3$): 3064, 3032, 2990, 2933, 2830, 1756, 1714, 1468, 1455, 1385, 1256, 1174, 1113, 1013 $cm^{-1}$.

$^1$H NMR (300 MHz, $CDCl_3$) 7.7–7.8 (m, 4H), 7.2 (m, 2H), 7.0 1. (m, 3H), 6.0–6.15 (m, 1H), 5.3 (m, 2H), 5.0 (m, 1H), 4.7 (m, 2H), 4.4 (dd, J=11.0, 5.3 Hz, 1H), 3.33 (s, 3H).

$^{13}$C NMR (75 MHz, $CDCl_3$) 170.0, 167.4, 135.8, 133.9, 131.6, 130.8, 128.4, 128.2, 126.8, 123.3 120.1, 82.1, 63.1, 57.3, 52.1.

Analysis: Calc'd for C, 69.03; H, 5.24; N, 3.83. Found: C, 68.88; H, 5.41; N, 3.98.

EXAMPLE 2

Part A: Preparation of (–)-1R,2R-Diamino-1N,2N-bis(2'-diphenylphosphinobenzoyl) cyclohexane, "6.28" or "(RR)-$L_B$".

To a dry flask containing alcohol or amine, excess 2-diphenylphosphinobenzoic acid, 5 mol % 4-dimethylaminopyridine in anhydrous solvent (THF or dichloromethane) under nitrogen was added dicyclohexylcarbodiimide. The yellow, chalky mixture was stirred at room temperature until thin layer chromatography indicted complete reaction.

The reaction mixture was filtered through a 2 cm pad of celite (wetted with dichloromethane) and the filter cake was washed twice with an equal volume of dichloromethane. Solvent was removed in vacuo and the residue was chromatographed on silica gel.

The reaction was run with (–)-1R,2R-diaminocyclohexane (0.1312 g, 1.149 mmol, Aldrich), 2-diphenylphosphinobenzoic acid (0.774 g, 2.528 mmol), and dicyclohexylcarbodiimide (0.521 g, 2.528 mmol) in dichloromethane (4 mL) for 9 h.

The residue was chromatographed twice on silica gel with 15–30% ethyl acetate/hexanes (gradient) to give the diamide 6.28 as a glass foam (0.2366 g, 29.8%).

Ligand 6.28: waxy solid precipitated from dichloromethane with hexanes, m.p. 80°–120° C.

$R_f$ 0.43 (50% ethyl acetate/hexanes).

IR (neat film from $CDCl_3$) 3303, 3070, 2935, 2857, 1955(w), 1887(w), 1817(w), 1645(s), 1538, 1478, 1434, 1328, 1306, 1162, 1091, 909 $cm^{-1}$.

$^1$H NMR ($CDCl_3$, 200 MHz) δ7.57(m, 2H), 7.15–7.26(m, 24H), 6.91(m, 2H), 6.31(bd, J=7.7Hz, 2H, N-H), 3.77(m, 2H), 1.87(m, 2H), 1.62(m, 2H), 0.9–1.3(m, 6H).

$^{13}$C NMR ($CDCl_3$, 50 MHz) δ169.46, 140.80(d, J=24.2 Hz), 137.96(d, J=11.8Hz), 137.88(d, J=12.3 Hz), 136.81(d, J=21.6 Hz), 134.34, 133.97(d, J=20.3 Hz), 130.23, 128.79, 128.66, 128.57, 128.51, 128.43, 127.63, 127.55, 53.68, 31.71, 24.41.

Analysis calcd. for $C_{44}H_{40}N_2O_2P_2$: C,76.51; H,5.83; N,4.06; P,8.97. Found: C,76.16; H,6.28;N,4.02; P,8.93.

$[\alpha]_D$=–46.7(±0.3)° (c2.366, dichloromethane).

Part B: 2-Phthalimidopent-E-3-en-1,5-diol

A dry 10 mL round bottomed flask was charged with tris(dibenzylideneacetone)dipalladium(O)chloroform complex (11.8 mg, 0.011 mmol), (+)-1R,2R-diamino-1N,2N-bis(2'-diphenylphosphinobenzoyl)cyclohexane (23.6 mg, 0.034 mmol), cesium carbonate (14.8 mg, 0.046 mmol), and phthalimide (73.6 mg, 0.500 mmol). The flask was then purged with argon and anhydrous THF (2 mL) was added. The resultant black-purple slurry was stirred at room temperature for 10 min, resulting in a clear red-orange solution.

To this mixture was added a solution of 4,5-epoxypent-E-2-En-1-ol (45.5 mg, 0.455 mol) in THF (2 mL) dropwise. The reaction was stirred at room temperature for 17 hours, or until thin layer chromatography (2/1:ethyl acetate/hexanes) indicated complete consumption of the epoxide alcohol. The solution was then gravity filtered and the resulting filtrate concentrated in vacuo to an orange oil which was directly chromatographed on silica gel with ethyl acetate to afford 98.3 mg (87%) of the product as a colorless oil.

$[\alpha]_D^{24.8}$=28.8°, c=1.966 ($CH_2Cl_2$)

$R_f$=0.25 (2/1:ethyl acetate/hexanes).

IR (neat): 3432, 1722, 1646, 1445, 1395, 1319, 1257, 1150, 1087, 1043, 842 $cm^{-1}$.

$^1$H NMR ($CDCl_3$, 300 MHz) δ: 7.80 (m, 2H), 7.70 (m, 2H), 6.04 (dd, J=15.6, 7.3 Hz, 1H), 5.87 (dt, J-15.6, 5.0 Hz, 1H), 4.91 (m, 1H), 4.11 (d, J-5.0 Hz, 2H), 4.06 (dd, J-11.6, 7.5 Hz, 1H), 3.94 (dd, J=11.6, 5.0 Hz, 1H), 2.80 (bs, 2H).

$^{13}$C NMR ($CDCl_3$, 75 MHz) δ: 168.52, 134.16, 133.94, 131.69, 124.87, 123.38, 62.83, 62.53, 54.85.

Mass spectrum m/e (rel intensity) 216(10), 199(55), 148 (100), 130(43).

HRMS calcd. for $C_{13}H_{13}NO_4$, 247.0845, (M-$H_2$COH) 216.0660, found 216.0654.

ee determined to be 83% by derivatization using (S)–(+) α-methoxyphenylacetic acid.

It is to be understood that while the invention has been described above in conjunction with preferred specific embodiments, the description and examples are intended to illustrate and not limit the scope of the invention, which is defined by the scope of the appended claims.

It is claimed:

1. A method for inducing chirality via an epoxide opening reaction, comprising:

using a vinylic epoxide as substrate, the epoxide having either structure

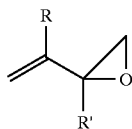

(Ep 1)

or

(Ep 2)

where R is H, alkyl, aryl, or a carboxylic acid derivative, a halide, a ketone, or a nitrile, and R' is H, alkyl, alkenyl, aryl, or a carboxylic acid derivative, a halide, a ketone, or a nitrile; and, inducing chirality by means of a bond forming reaction between the epoxide substrate and a chiral ligand, said reaction occurring in the presence of a transition metal complex, the ligand comprising a chiral backbone to which is bound two metal binding moieties, each of the metal binding moieties having the structure

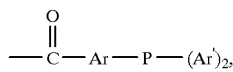

where Ar and Ar' each is the same or different and each is an aryl with a single ring or with a fused ring, and wherein the chiral backbone is derived from a chiral bis-alcohol or a chiral bis-amine and each metal binding moiety is attached by an ester linkage to each of the alcohol functionalities in the chiral bis-alcohol or is attached by an amide linkage to each of the amine functionalities in the chiral bis-amine.

2. The method as in claim 1 wherein the single or fused ring aryl includes a heteroatom.

3. The method as in claim 2 wherein the heteroatom is selected from the group consisting of nitrogen, oxygen, or sulphur.

4. The method as in claim 2 wherein when the fused ring aryl includes a heteroatom then the metal binding moiety therewith has the structure selected from the group consisting of

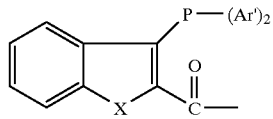

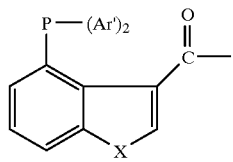

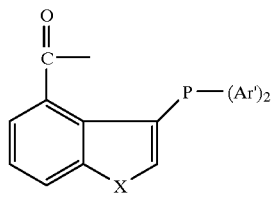

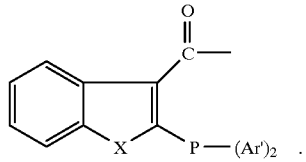

5. The method as in claim 1 wherein the ligand has the structure

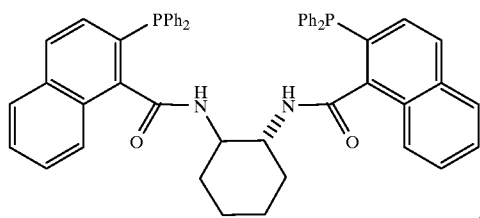

6. The method as in claim 1 wherein the ligand has the structure

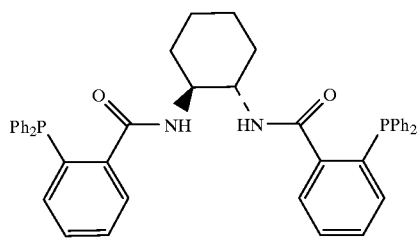
7. The method as in claim 1 wherein the ligand has $C_2$ symmetry.
8. The method as in claim 1 wherein a vinylglycinol derivative is formed in high enantiomeric purity from the epoxide substrate.
9. The method as in claim 8 wherein the vinylglycinol derivative is a phthalimide derivative.
* * * * *